US 6,683,779 B2

(12) United States Patent
Ober (10) Patent No.: US 6,683,779 B2
(45) Date of Patent: Jan. 27, 2004

(54) PERSONAL BODY GROUNDING SYSTEM (75) Inventor: A. Clinton Ober, Ventura, CA (US)

(73) Assignee: Earth Tether International Corporation, West Covina, CA (US)

( * ) Notice: Subject to any disclaimer, the term of this patent is extended or adjusted under 35 U.S.C. 154(b) by 353 days.

(21) Appl. No.: 09/808,537

(22) Filed: Mar. 14, 2001

(65) Prior Publication Data
US 2002/0027761 A1 Mar. 7, 2002

Related U.S. Application Data
(60) Provisional application No. 60/189,154, filed on Mar. 14, 2000, and provisional application No. 60/189,185, filed on Mar. 14, 2000.

(51) Int. Cl.[7] .............................................. H02H 47/00
(52) U.S. Cl. ...................................... 361/220; 361/212
(58) Field of Search ................................ 361/212, 220, 361/92

(56) References Cited

U.S. PATENT DOCUMENTS

| 1,607,140 | A |   | 11/1926 | Wappler |         |
|-----------|---|---|---------|---------|---------|
| 2,753,491 | A |   | 7/1956  | Legge   | 317/2   |
| 3,917,979 | A |   | 11/1975 | Volk, Jr. | 317/18 |
| 4,373,175 | A |   | 2/1983  | Mykkanen | 361/220 |
| 4,415,946 | A |   | 11/1983 | Pitts    | 361/212 |
| 4,450,498 | A |   | 5/1984  | Siegal   | 361/212 |
| 4,596,053 | A |   | 6/1986  | Cohen et al. | 361/223 |
| 4,680,668 | A | * | 7/1987  | Belkin   | 361/220 |
| 4,945,447 | A |   | 7/1990  | Aronson  | 361/212 |
| 5,515,234 | A |   | 5/1996  | Frazier  | 361/212 |
| 5,548,469 | A |   | 8/1996  | Adams    | 361/220 |
| 5,715,536 | A | * | 2/1998  | Banks    | 2/69    |

OTHER PUBLICATIONS

Title: Elf Electric and Magnetic Fields In the Bedplace of Children Diagnosed with Leukaemia; Author: Roger William Coghill; Date: 1996; 15 pages.
Title: Health Effects from Exposure to Power–Line Frequency Electric and Magnetic Fields: Date: May 04, 1999; 73 pages; Author: Dr. Kenneth Olden.

* cited by examiner

Primary Examiner—Stephen W. Jackson
(74) Attorney, Agent, or Firm—Kelly Bauersfeld Lowry & Kelley, LLP (57) ABSTRACT A personal grounding system for collecting and removing unnatural electrical charges from a human body includes a grounding pad having a layer of carbon fibers, and a conductor substantially extending across the layer in conductive contact with the carbon fibers. A ground lead is conductively coupled to the grounding pad conductor at one end thereof and conductively coupled to a grounded anchor at a second end thereof. Preferably, the grounded anchor is placed directly into the earth, although in certain applications constitutes a metal grounding component. The system may include a wall plate in conductive connection with the grounded anchor. The ground lead is removably attached to the wall plate via a connector attached thereto. The grounding pad may be configured to be a sleeping pad, seat pad, or strap or patch attachable to the human body.

20 Claims, 5 Drawing Sheets

PERSONAL BODY GROUNDING SYSTEM

RELATED APPLICATION

This application claims priority from provisional application Serial No. 60/189,154, filed Mar. 14, 2000 and provisional application Serial No. 60/189,185, filed Mar. 14, 2000.

BACKGROUND OF THE INVENTION

The present invention relates to grounding systems. More particularly, the present invention relates to a personal grounding system for collecting and removing electrical charges from a human body.

When the human body makes physical contact with the ground, as was the case throughout evolution, the body naturally attenuates the negative electrical properties of the earth and becomes electrically neutral like the earth. In this state any extraneous electricity that is present in or on the body is naturally dissipated and thereafter prevented from accumulating in or on the body. Due to the common modern world practice of wearing insulating rubber soled shoes and living in environments that hold the body in free space above the earth, humans by and large no longer make contact with the earth. As a result, internally generated body electricity is not being naturally dissipated by the negative electrical properties of the earth. Consequently, this stored body electricity now interferes with normal cellular communications and thereby interferes with the self-regulating and self-healing mechanisms of the body, which in turn create stress and disorder in the body.

Further, with loss of natural ground contact, electric and magnetic fields (EMFs) now create weak electric currents in the body. Scientists and researchers in the field of electromagnetic radiation and bio-electromagnetics have confirmed that these exogenous electrical fields interfere with the endogenous fields of the body and produce adverse physical and behavioral changes. It has been found that the unnatural presence of these continuously generated electrostatic charges on the body adversely affects the bioelectrical nervous system of the body and consequently causes body muscles to become and remain abnormally tense. Prolonged exposure to the electrostatic charges can result in muscle stiffness and back pain. In this physiologically stressed state, blood pressure rises, heart rate increases and the digestive process slows. It is believed that the unnatural presence of electrostatic charges on the body may also have a correlation with certain diseases.

While in bed everyone carries a measurable electric field charge on their body due to electric fields continuously radiating from the electrical wiring in the walls and the cords and components of electrical devices within modern houses. The levels of electric field charges on the body vary from a few hundred millivolts to in excess of ten volts. For reference purposes, the natural biological voltage of the body, as a whole, is zero.

Research suggests that the normal sleep processes of the body are affected by the continuous exposure of the body to electric fields throughout the night. The National Sleep Foundations 1999 Sleep in America poll found that more than sixty percent of Americans now experience sleep problems a few nights a week or more and fifty-six percent experience one or more symptoms of insomnia, including difficulty falling asleep, waking during the night, waking too early, or waking feeling unrefreshed. The continuous exposure to electric fields throughout the night is, based upon research and test results, the cause of many modern sleep problems.

While driving a vehicle, the combination of road vibration and related personal body movement cause continuous contact and separation as well as friction between personal clothing, the vehicle seat materials, and the padding within the vehicle seat. The repetitive contact creates electrostatic charges which migrate to and accumulate on the body. Based upon research and test results, the consequence of bioelectrical stress from static electricity is a cause of drivers becoming abnormally tense, irritable and fatigued while driving.

The American Stress Institute, has reported that 75% of all visits to a primary care physician are for stress related health disorders. Stress is often defined as a state of continuous anxiety and nervousness in which muscles become and remain tensed. Stress is the result of excess electrical stimuli in the body, which block and disrupt the normal production and flow of bioelectrical communications between nerve cells. The primary causes of excess electrical stimuli in the body is the over-stimulation of nerves from emotional responses to work pressure or life situations, exposure to electric and magnetic fields (EMFS), radio frequencies, static electricity and the like. While the immediate consequence of excess or extraneous electricity in the body is tense and tight muscles, the long term effects are believed to be a contributor to various diseases and immune system disorders. There is an increasing body of research which indicates that removal of extraneous electrostatic charges on a human body reduces stress and pain.

Accordingly, there is a need for a grounding system which collects and removes electrical charges from a human body. Such a grounding system should be capable of being used while sleeping, during prolonged periods of sitting, as well as being targeted to an area of the body. The present invention fulfills these needs and provides other related advantages.

SUMMARY OF THE INVENTION

The present invention relates to a personal grounding system for collecting and removing excess internal and extraneous electrical charges from a human body in order to return the body to its natural electrically neutral state. The system generally comprises a grounding pad having a ground lead extending therefrom and conductively coupled to a grounded anchor. The grounding pad includes a mesh layer substrate comprised of a plurality of carbon fibers. Typically, the grounding pad comprises between 10% and 20% carbon fibers. A conductor substantially extends across the substrate and in conductive contact with the carbon fibers. The ground lead has a first end which is conductively coupled to the grounding pad conductor.

The grounding pad is configured to make field contact or conductive contact with the human body. In this regard, the grounding pad can comprise a sleeping pad, which in one form is securely positionable on a mattress. The grounding pad may alternatively comprise a strap which is securable around a human body member, such as a foot or ankle. The ground pad may also comprise a patch which is attachable to an area of the human body. Such a patch includes a peel away strip overlying an adhesive layer which is adhered to the area of the human body to which the patch is to be attached. The grounding pad may also comprise a seat pad, for use on a desk or computer chair or the seat of a vehicle.

Preferably, the grounded anchor is placed directly into the earth. However, in certain circumstances, such as when the grounding pad comprises a vehicle seat pad, the grounding anchor comprises a metal grounding component, such as a metal component of a vehicle.

The system may include a wall plate which is in conductive connection with the grounded anchor. The ground lead includes a connector attached to an end thereof which is capable of removable attachment with the wall plate. The system may also include a meter for reading the electrical charges collected from the human body, and a fuse to prevent electrical shock.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figures 1, 2:
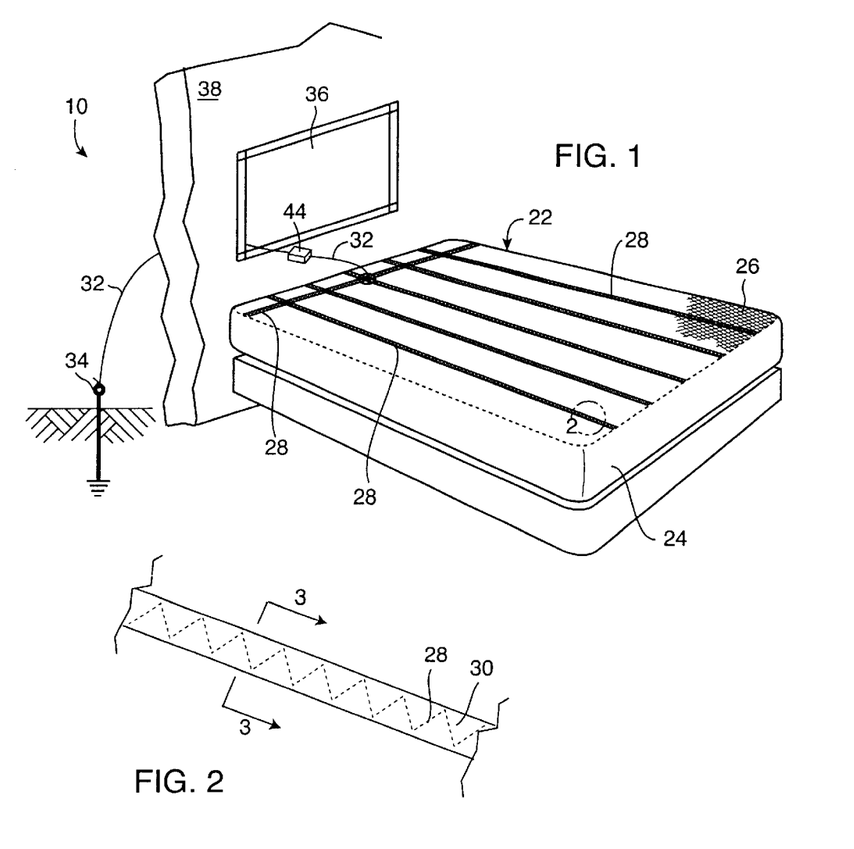
FIG. 1 is a schematic view of a personal grounding system embodying the present invention, the system comprising a sleeping pad positioned on a mattress and directly connected to an earth ground anchor.
FIG. 2 is an enlarged view of area "2" of FIG. 1, illustrating a conductor extending through a grounding pad of the system.
Figure 3:
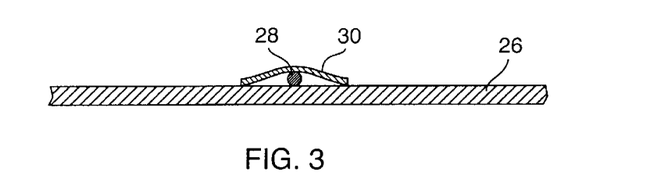
FIG. 3 is a cross sectional view taken generally along line 3—3 of FIG. 2, illustrating the conductor in contact with a carbon fiber mesh.
Figure 4:
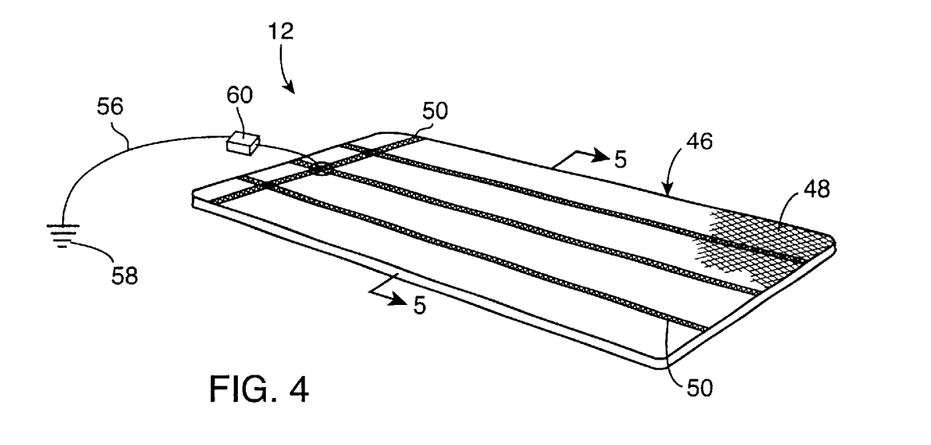
FIG. 4 is a perspective view of another personal grounding system in the form of a sleeping pad.
Figure 5:
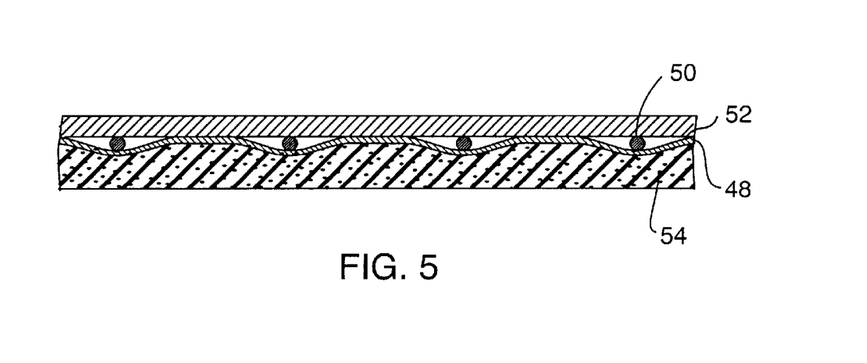
FIG. 5 is a cross sectional view taken generally along the line 5—5 of FIG. 4, illustrating the components of the sleeping pad.
Figure 6:
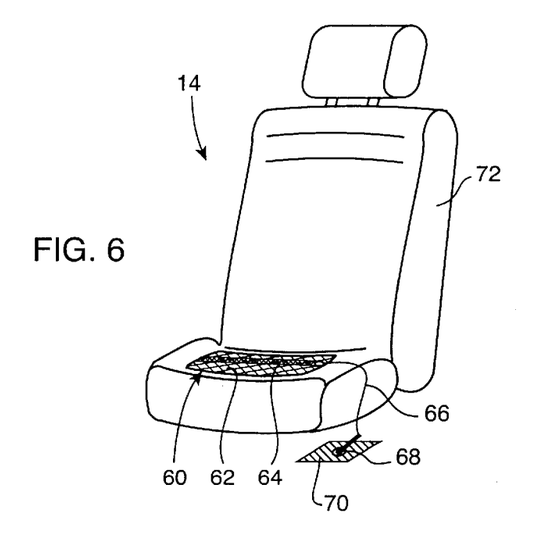
FIG. 6 is a perspective view of a vehicle seat having a personal grounding system in accordance with the present invention associated therewith.
Figure 7:
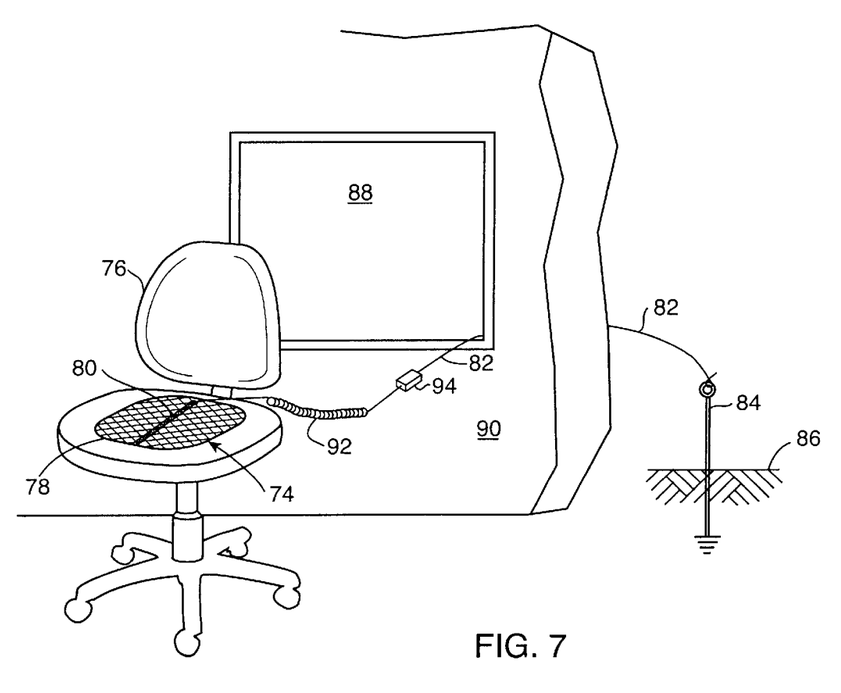
FIG. 7 is a partially fragmented perspective view of an office chair having a grounding pad placed thereon, and a ground lead extending from the grounding pad to a grounded anchor placed in the earth.
Figure 8:
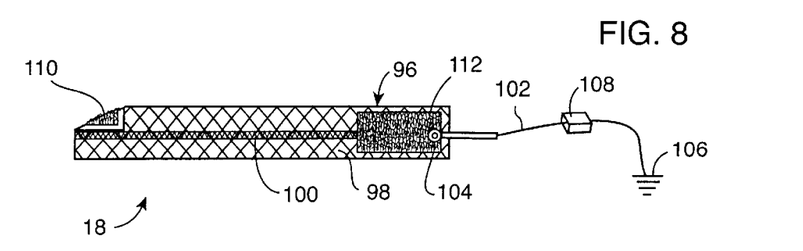
FIG. 8 is a perspective view of a grounding pad in the form of a strap used in accordance with the present invention.
Figure 9:
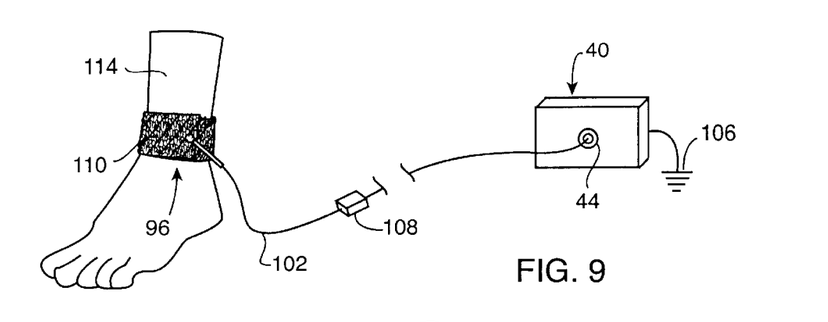
FIG. 9 is a perspective view of the ground strap of FIG. 8 secured to an ankle of a user, and connected to a wall plate in conductive connection with a grounded anchor.
Figure 10:
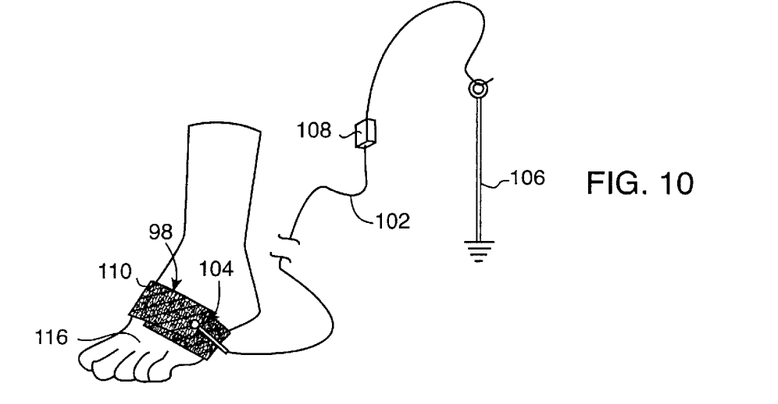
FIG. 10 is a perspective view of the grounding strap of FIG. 8 attached to a foot of a user, and connected to a grounded anchor placed in the earth.

As shown in the drawings for purposes of illustration, the present invention is concerned with a system for grounding human bodies, generally referred to by the reference number 10 in FIGS. 1–3, generally referred to by the reference number 12 in FIGS. 4–5, generally referred to by the reference number 14 in FIG. 6, generally referred to by the reference number 16 in FIG. 7, generally referred to by the reference number 18 in FIGS. 8–10, and generally referred to by the reference number 20 in FIGS. 11–15. The system 10–20 is designed to collect and remove electrical charges from a human body.

With reference to FIGS. 1–3, the system 10 includes a grounding pad 22 in the form of a sleeping pad which is securely positionable on a mattress 24. The grounding pad 22 can be positioned under a fitted sheet or bottom sheet of the mattress 24. The providing pad 22 may also include an elastic extension (not shown) for direct attachment to the mattress 24. The grounding pad 22 is sufficiently large enough that a sleeping body is effectively and conveniently grounded regardless of what position the person may normally sleep in. The grounding pad 22 includes a mesh layer substrate 26 which is comprised of a plurality of carbon fibers. Typically, this substrate 26 comprises 87% polyester and 13% carbon-suffused monofilament nylon knitted into a conductive grid pattern. Although 13% carbon fiber content is preferred, the grounding pad 22 carbon fiber content may vary, such as between 10% and 20% carbon fibers. One or more conductors 28 substantially extend across the carbon fiber substrate 26 so as to be in conductive contact with the carbon fibers. Although as few as one conductor 28 can be used, preferably a plurality of conductors 28 are used and spaced from one another and interconnected in order to effectively conduct the electrostatic charges from the carbon fiber substrate 26.

As shown in FIGS. 2 and 3, the conductors 28 are placed between substrate 26 and preferably sewn to substrate 26 in a zig-zag configuration so as to optimize the conductive contact with the carbon fiber substrate 26. However, the conductors 28 configuration is not limited to such. A fabric strip 30 overlies the conductor 28 in order to prevent contact with conductor and the person sleeping thereon. The fabric strip 30 may comprise a conductive cooper clad nylon fabric strip or a stranded copper wire for the purpose of making additional conductive contact with the carbon fibers contained in the substrate 26. The grounding pad 22 can include additional layers of fabric, foam or felt for comfort and support purposes.

Referring back to FIG. 1, a ground lead 32 is connected at a first end thereof to a conductor 28 of the grounding pad 22. As illustrated in FIG. 1, preferably the ground lead 32 is connected to a conductor 28 which interconnects several other conductors 28. The ground lead 32 can be coupled to the grounding pad conductor 28 in various ways. For example, a rivet may be placed through the portion of the grounding pad 22 containing the conductor 28. The ground lead 32 would include a connector, such as a snap-fit connector, which could be snapped onto the rivet. The ground lead 32 is comprised of a conductive material, such as cooper wire. The ground lead 32 is of sufficient length to extend from the grounding pad 22 to a grounded anchor 34 which is preferably placed directly into the earth. The ground lead 32 may extend from the grounding pad 22 and through a window 36 or other aperture of a wall 38 and into contact with the ground anchor 34.

Although the ground anchor 34 can comprise any ground, the ground connection is typically not normal electric grounds like electrical outlet grounds and water pipes as these carry resistance levels that maintain abnormally high electric voltage levels on the body. For this reason, the invention preferably uses a dedicated direct earth ground by placing the ground anchor 34 directly in the earth and using it as a ground connection. The use of such a ground anchor 34 effectively neutralizes the electrical charges.

Alternatively, the ground lead 32 is of sufficient length to attach to a wall plate 40, as illustrated in FIG. 9, which is conductively connected to the grounded anchor 34. The end of the ground lead 32 preferably includes a connector 44 which can be removably attached to the wall plate 40. Although the connector 42 can comprise a plug, such as a banana clip, for insertion into an outlet-like aperture of the wall plate 40, preferably the connector 42 comprises a snap-fit connector of the circular or ring variety which can be snapped onto a mating member of the wall plate 40 so that children do not accidentally insert the connector 42 into an electrical socket.

A meter or fuse 44 may be associated with a system 10, and typically installed within the ground lead 32, as illustrated in FIG. 1. The meter is intended to read electrical charges on 22, the human body before and after being grounded. The fuse 44 is intended to prevent electrical shock, such as in the event lightening strikes or electrification of the ground anchor 34 and ground lead 32, or a faulty wiring extending from a lamp and the like contacting the grounding pad 22.

Although several fuses may be adequately used, a $\frac{1}{100}$ amp fuse is utilized for minimum protection. This level of protection is sufficient to prevent physical harm to the body lying on the grounding pad 22. A fuse 44 is preferred for protection over a resistor due to the fact that the resistance of a resistor causes some level of electric field charges to be retained on the body.

With reference now to FIG. 4, another system 12 is illustrated wherein the grounding pad 46 comprises sleeping pad which can be slept on directly, under a sleeping bag, or the like without the need for a mattress 24. The grounding pad 46 is similar to the grounding pad 22 described above in that it includes a mesh layer substrate 48 containing the plurality of carbon fibers formed in a grid as described above. The grounding pad 46 also includes a plurality of conductors 50 similar to that described above. As illustrated in FIG. 5, an adhesive layer 52 underlies the mesh substrate 48 and conductor 50 to bond substrate to foam pad 54. The grounding pad 46 includes a foam base 54 for cushioning purposes. Similar to that described above, the system 12 includes a ground lead 56 interconnected between a conductor 50 of the grounding pad 46 and a grounded anchor 58 which is preferably placed directly into the earth, although the ground lead 56 may be attached to a wall plate 40 as illustrated in FIG. 9. The system 12 also includes a fuse 60 for ground fault protection. Although this embodiment can also be placed on a mattress 24, it is designed such so as to be portable and used directly on a hard surface such as a floor or the ground.

With reference now to FIG. 6, another personal grounding system 14 is illustrated which is particularly adapted for use in vehicles. The system 14 includes a grounding pad 60 which is sized so as to be placed on a car or truck seat. The grounding pad 60 is similar to those described above in that it includes a mesh layer substrate 62 of conductive carbon fibers. Due to its size, typically only one conductor 64 is required. The conductor 64 substantially extends from one end of the grounding pad 60 to the other so as to contact the carbon fibers within the substrate 62. A ground lead 66 extends from the conductor 64. The ground lead includes a connector 68, often an alligator clip or the like, which is attachable to a metal component 70 of the vehicle which serves as a ground. Preferably, the metal component 70 should comprise a metal member under the seat 72 which is conductively connected to the chassis of the vehicle frame. The system 14 includes a meter or fuse (not shown), although the need for a fuse is greatly diminished as the potential for electrocution within the vehicle is very low.

The grounding pad 60 may include a rubber layer for supporting structure to the pad 60. The rubber layer would be of sufficient weight to maintain the grounding pad 60 in position on the seat. The grounding pad 60 may also include a fabric material having a light layer of dry adhesive for securely holding the grounding pad 60 in place on the seat. Alternatively, the grounding pad 60 could be molded directly to the top layer of the seat 72 during manufacture. As can be appreciated by the reader, the size of the grounding pad 60 may vary depending upon the type and size of the vehicle seat the pad 60 is intended to be used on. Although electrical contact is not necessarily made directly between the body of the user and the ground pad 60, electrical contact is made either via body perspiration on the person's clothing and/or by the negative electrical field that is created by the grounding pad 60. This concept applies to other embodiments where the person's body is not in direct contact with the grounding pad.

With reference now to FIG. 7, another personal grounding system 16 is illustrated which is similar to that shown in FIG. 6. The system 16 includes a ground pad 74 in the form of a seat pad which is positionable on a computer or office chair 76 or the like. As described above, the grounding pad 74 includes a carbon fiber mesh substrate 78 having one or more conductors 80 extending substantially across the substrate 78. Due to its size, typically only one conductor 80 is necessary. A ground lead 82 is coupled to the conductor 80 of the grounding pad 74 at one end thereof, and coupled to a ground anchor 84 at an opposite end thereof. As described above, the ground anchor 84 is preferably placed directly into the ground, although a wall unit 40, as illustrated in FIG. 9, can be used to connect to the ground anchor 84 when the distance between the chair 76 and the earth 86 is too great or otherwise not feasible. The ground lead 82 is of sufficient length so as to extend between the grounding pad 74 placed on the chair 76 and the wall plate 40 or ground anchor 84. The ground lead 82 may extend through a window 88 or other aperture of a wall 90 to reach the ground anchor 84. As an office chair 76 is typically moved somewhat during use, the ground lead 82 preferably includes an expandable coiled section 92 permitting the chair 76 to be moved towards and away from the wall 90 with minimal disruption to the placement of the grounding pad 74 thereon. The system 16 may include a meter for reading the electrical charges collected from the grounding pad 74, and thus the body placed thereon, as well as a fuse 94 to prevent electrical shock and electrocution as described above.

Referring now to FIG. 8, yet another personal grounding system 18 is illustrated. The system 18 includes a grounding pad in the form of a strap 96 which is sized such so as to be placed around a body member, such as an ankle 114 or foot 116 as illustrated in FIGS. 9 and 10. The strap 96, similar to the grounding pads described above, includes a carbon fiber mesh substrate layer 98 having a conductor 100 extending substantially the length thereof. The carbon fibers within the substrate mesh layer 98 preferably overlap one another and form a grid, the conductor 100 coming into conductive contact with the carbon fiber layer 98 such as that described above.

The system 18 includes a ground lead 102 which is coupled to the conductor 100 of the strap 96. Preferably, the ground lead 102 includes a connector 104 which can be removably connected to or coupled with the conductor 100. For example, the connector 104 can comprise a snap-fit ring or the like which is mated with an end of a rivet, similar to that illustrated in FIG. 13. It will be appreciated by the reader that other methods of coupling and connecting the ground lead 102 to the conductor 100 are possible as well. The ground lead 102 is of sufficient length to connect to a ground anchor 106. If the person wearing the strap 96 intends to be immobile during use, the ground lead 102 may be fairly short. However, if the user intends to be more mobile during use of the invention, the ground lead 102 is of sufficient length to permit the person to walk and move as necessary.

The system 18 preferably includes a fuse 108, typically interposed within the ground lead 102, as a safety precaution against electrical shock or electrocution. A backside of the strap 96 is attached to a strip of hook and loop tape 110, such as by adhesion. Another patch of hook and loop tape 112 is attached to an end of the front side over the ground lead 102 connection of the strap 96 so as to engage the hook and loop tape 110 of the back side to secure the strap 96 to a body member of a user. As illustrated in FIGS. 9 and 10, the strap 96 can be secure around an ankle 114 or foot 116 of the user and grounded through ground lead 102 to a wall plate 40 or directly to the ground anchor 106. Preferably, the strap 96 is attached to an exposed portion of the body to optimize the collection and removal of electrical charges from the body. Using this system 18, a user can apply the strap 96 and do house chores or the like while realizing the benefits of the invention.

With reference now to FIGS. 11–14, another personal grounding system 20 is illustrated in the form of a patch 118 which is attachable to an area of the human body to be treated. The patch 118 includes a carbon fiber mesh layer substrate 120 as described above. Due to the fact that the patch 118 is often of relatively small size, a conductive rivet 122 is imbedded within the patch 118 and serves as the conductor. However, it is to be understood that a wire or strip conductor as described above can be incorporated into this system 20 as well.

Figure 11:
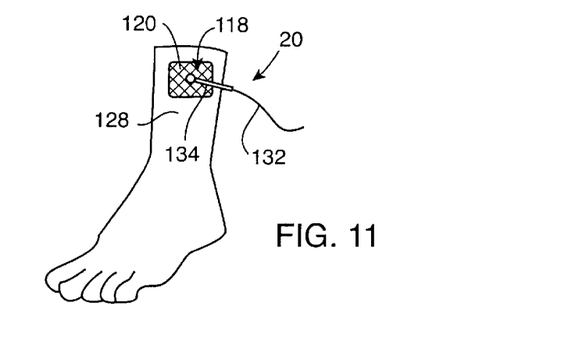
FIG. 11 is an elevational view of a grounding patch attached to a leg of a user.
Figure 12:
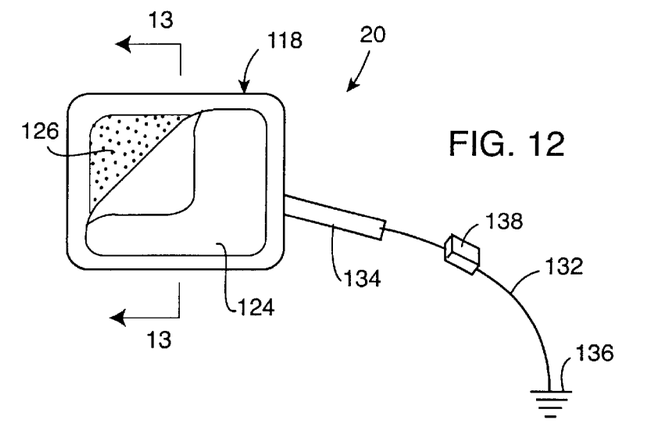
FIG. 12 is a perspective view of the patch of FIG. 11, illustrating the removal of a peel away strip therefrom.
Figure 13:
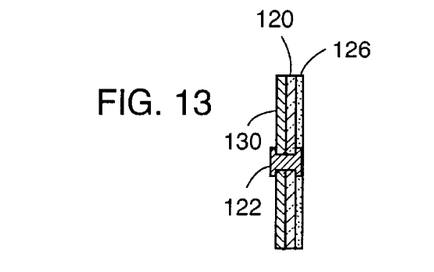
FIG. 13 is a cross sectional view taken along line 13—13 of FIG. 12.
Figures 14, 15:
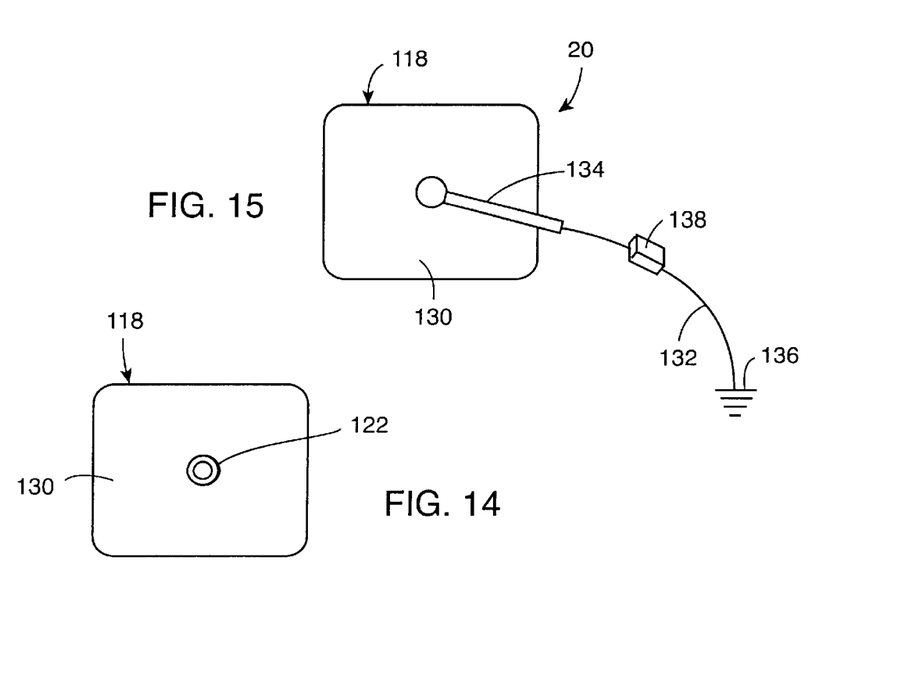
FIG. 14 is a top view of the patch of FIGS. 11 and 12, illustrating a rivet extending from a surface thereof.
FIG. 15 is a top view of the patch of FIG. 14, illustrating a snap-fit connector attached to a ground lead and the rivet of the patch.

Referring now to FIG. 12, the patch 118 includes a peel away strip 124 which can be removed to expose a conductive adhesive layer 126 which holds the patch 118 in place on the body, such as the leg 128 illustrated in FIG. 11. The carbon fiber substrate layer 120 is disposed under the conductive adhesive layer 126. A protective covering 130, such as fabric or plastic, overlies the carbon fiber substrate 120 and forms a backside of the patch 118. A ground lead 132 is coupled to the conductor rivet 122 via a connector 134 designed to mate with the rivet 122. Typically, the connector 134 comprises a snap-fit ring or the like which can be removably connected to the rivet 122 by pressing and snapping the connector 134 onto an exposed portion of the rivet 122. The rivet 122 is disposed within the patch 118 such that it contacts or extends through the carbon fiber mesh substrate 120 and extends beyond the protective covering 130 for attachment to the ground lead connector 134. Preferably, the rivet 122 lies flush with, or within, the adhesive layer 126 so as not to cause irritation or discomfort to the wearer of the patch 118. As described above, the ground lead 132 extends to an appropriate connection to a ground anchor 136 which is preferably placed directly into the earth. Similarly, the ground lead 132 can be attached to a wall outlet 40, which is in turn directly connected to the ground anchor 136. The system 120 preferably also includes a fuse 138 to prevent electrical shock or electrocution as described above.

In use, the peel away strip 124 is removed from the patch 118 and the adhesive layer 126 pressed into contact with the body area having muscle tension, fatigue or pain. The ground lead connector 134 is attached to the rivet 122 at one end thereof, and grounded anchor 136 at the other end thereof. Electrostatic charges are collected by the conductive adhesive 126 and carbon fiber substrate 120 of the patch 118 and directed through the ground lead 132 and into the earth through ground anchor 136. The removal of such electrostatic charges is tested and known to reduce chronic pain in a localized area. The patch 118 is advantageous as the user can target a very specific area of the body.

Although several embodiments of the invention have been described in detail for purposes of illustration, various modifications may be made without departing from the spirit and scope of the invention. Accordingly, the invention is not to be limited, except as by the appended claims.

What is claimed is:

1. A personal grounding system for collecting and removing electrical charges from a human body, comprising:

a grounding pad comprising a sitting or sleeping pad and including a mesh layer substrate comprised of a plurality of electrically conductive fibers, and a conductor substantially extending across the substrate in conductive contact with the fibers, the grounding pad being configured to make field or conductive contact with the human body;

a ground lead having a first end conductively coupled to the grounding pad conductor; and a grounded anchor conductively coupled to a second end of the ground lead.

2. The system of claim 1, wherein the fibers of the grounding pad comprises between 10% and 20% carbon fibers.

3. The system of claim 1, wherein the grounded anchor is placed directly into the earth.

4. The system of claim 1, wherein the grounding pad comprises a sleeping pad securely positionable on a mattress.

5. The system of claim 1, wherein the grounding pad comprises a sitting pad positionable on a vehicle seat, and wherein the grounding anchor comprises a metal component of a vehicle.

6. The system of claim 1, including a fuse associated with the system to prevent electrical shock to the human body.

7. The system of claim 1, including a connector attached to an end of the ground lead and capable of removable attachment with a wall plate in conductive connection with the grounding anchor.

8. The system of claim 1, including a meter associated with the system for reading the electrical charges on or collected from the human body.

9. A personal grounding system for collecting and removing electrical charges from a human body, comprising:

a grounding pad comprised of a sitting or sleeping pad and including a mesh layer substrate comprised of a plurality of carbon fibers, and a conductor substantially extending across the substrate in conductive contact with the carbon fibers, the grounding pad being configured to make field or conductive contact with the human body resting thereon;

a ground lead having a first end conductively coupled to the grounding pad conductor;

a grounded anchor conductively coupled to a second end of the ground lead and placed directly into the earth; and a fuse disposed between the first end of the ground lead and the grounded anchor for preventing electrical shock to the human body while effectively neutralizing electrical charge therefrom;

wherein the carbon fibers comprise between 10% and 20% of the grounding pad.

10. The system of claim 9, wherein the sleeping pad is securely positionable on a mattress.

11. The system of claim 9, including a connector attached to an end of the ground lead and capable of removable attachment with a wall plate in conductive connection with the grounding anchor.

12. The system of claim 9, including a meter associated with the system for reading the electrical charges on or collected from the human body.

13. A personal grounding system for collecting and removing electrical charges from a human body, comprising:

a grounding pad comprising a strap securable around a human body member and including a mesh layer substrate comprised of a plurality of carbon fibers, and a conductor substantially extending across the substrate in conductive contact with the carbon fibers, the grounding pad being configured to make field or conductive contact with the human body;

a ground lead having a first end conductively coupled to the grounding pad conductor;

a grounded anchor conductively coupled to a second end of the ground lead and placed directly into the earth; and a fuse disposed between the grounded anchor and the conductor to prevent electrical shock to the human body while effectively nuetralizing electrical charges therefrom.

14. The system of claim 13, wherein the grounding pad comprises between 10% and 20% carbon fibers.

15. The system of claim 13, including a connector attached to an end of the ground lead and capable of removable attachment with a wall plate in conductive connection with the grounding anchor.

16. The system of claim 13, including a meter associated with the system for reading the electrical charges on or collected from the human body.

17. A personal grounding system for collecting and removing electrical charges from a human body, comprising:

a grounding pad comprising a conductive adhesive layer, a peel away strip removably attached to one surface of the adhesive layer, and a mesh layer substrate attached to an opposite surface of the adhesive layer and comprised of a plurality of carbon fibers, and a conductor substantially extending across the substrate in conductive contact with the carbon fibers, wherein the grounding pad is configured to be removably attached to a portion of a human body to make field or conductive contact therewith;

a ground lead having a first end conductively coupled to the grounding pad conductor;

a grounded anchor conductively coupled to a second end of the ground lead; and a fuse disposed between the first end of the ground lead and the grounded anchor for preventing electrical shock to the human body while effectively neutralizing charges thereto.

18. The system of claim 17, wherein the grounding pad comprises between 10% and 20% carbon fibers.

19. The system of claim 17, including a connector attached to an end of the ground lead and capable of removable attachment with a wall plate in conductive connection with the grounding anchor.

20. The system of claim 17, including a meter associated with the system for reading the electrical charges on or collected from the human body.

* * * * *